US009926365B2

(12) United States Patent
Qian et al.

(10) Patent No.: US 9,926,365 B2
(45) Date of Patent: Mar. 27, 2018

(54) METHODS FOR REDUCING GLYCOPROTEIN AGGREGATION (71) Applicant: BRISTOL-MYERS SQUIBB COMPANY, Princeton, NJ (US)

(72) Inventors: Yueming Qian, Manlius, NY (US); Sarwat Khattak, Cary, NC (US); Zhengjian Li, Sudbury, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 74 days.

(21) Appl. No.: 14/410,709

(22) PCT Filed: Jun. 27, 2013

(86) PCT No.: PCT/US2013/048105
§ 371 (c)(1),
(2) Date: Dec. 23, 2014

(87) PCT Pub. No.: WO2014/004780
PCT Pub. Date: Jan. 3, 2014

(65) Prior Publication Data
US 2015/0322139 A1 Nov. 12, 2015

(51) Int. Cl.
C07K 14/705 (2006.01)
C07K 16/18 (2006.01)
(52) U.S. Cl.
CPC ........ C07K 16/18 (2013.01); C07K 14/70521 (2013.01); C07K 2317/41 (2013.01); C07K 2317/52 (2013.01); C07K 2317/94 (2013.01); C07K 2319/30 (2013.01)
(58) Field of Classification Search
CPC ............ C07K 2317/41; C07K 2317/52; C07K 2317/53; C07K 14/705; C07K 14/70503; C07K 14/70521
See application file for complete search history.

(56) References Cited

U.S. PATENT DOCUMENTS

| 7,094,874 | B2 | 8/2006 | Peach et al. |
| 7,332,303 | B2 | 2/2008 | Schilling et al. |
| 7,541,164 | B2 | 6/2009 | Schilling et al. |
| 2004/0137581 | A1 | 7/2004 | Aguinaldo et al. |
| 2006/0234917 | A1 | 10/2006 | Ambrose et al. |
| 2009/0252749 | A1* | 10/2009 | Leister ............. C07K 14/70521 424/178.1 |
| 2010/0166774 | A1 | 7/2010 | Dali et al. |

FOREIGN PATENT DOCUMENTS

| EP | 1 449 849 A2 | 8/2004 |
| WO | WO 2007/076032 A2 | 7/2007 |
| WO | WO 2008/143954 A2 | 11/2008 |
| WO | WO 2010/085682 A2 | 7/2010 |
| WO | WO 2010/128145 A1 | 11/2010 |
| WO | WO 2012/170938 A1 | 12/2012 |
| WO | WO2013/169338 A1 * | 11/2013 |

OTHER PUBLICATIONS

Biller, et al., "Early steps in O-linked glycosylation and clustered O-linked glycans of herpes simplex virus type 1 glycoprotein C: effects on glycoprotein properties", Glycobiology, 2000, vol. 10, No. 12, pp. 1259-1269.
Broach, et al., "Construction of High Copy Yeast Vectors Using 2-μm Circle Sequences", Methods in Enzymology, 1983, vol. 101, pp. 307-325.
Itakura et al. "Expression in Escherichia coli of a Chemically Synthesized Gene for the Hormone Somatostatin", Science, vol. 198, pp. 1056-1063.
Clarke, et al., "Selection Procedure for Isolation of Centromere DNAs from Saccharomyces cerevisiae", Methods in Enzymology, 1983, vol. 101, pp. 300-307.
Cohen, et al., "Nonchromosomal Antibiotic Resistance in Bacteria: Genetic Transformation of Escherichia coli by R-Factor DNA", Proc. Nat. Acad. Sci. USA, Aug. 1972, vol. 69, No. 8, pp. 2110-2114.
Fiers, et al., "Complete nucleotide sequence of SV40 DNA", Nature, May 11, 1978, vol. 273, pp. 113-120.
Goeddel, et al., "Synthesis of human fibroblast interferon by E. coli", Nucleic Acids Research, 1980, vol. 8, No. 18, pp. 4057-4074.
Hess, et al., "Cooperation of Glycolytic Enzymes", 1968, vol. 7, pp. 149-167.
Hitzeman, et al., "Isolation and Characterization of the Yeast 3-Phosphoglycerokinase Gene (PGK) by an Immunological Screening Technique", The Journal of Biological Chemistry, Dec. 25, 1980, vol. 255, No. 24, pp. 12073-12080.
Holland, et al., "Isolation and Identification of Yeast Messenger Ribonucleic Acids Coding for Enolase, Glyceraldehyde-3-phosphate Dehydrogenase, and Phosphoglycerate Kinase", Biochemistry, 1978, vol. 17, No. 23, pp. 4900-4907.
Hossler, et al., "Optimal and consistent protein glycosylation in mammalian cell culture", Glycobiology, 2009, vol. 19, No. 9, pp. 936-949.
Jing, et al., "Sialylation Enhancement of CTLA4-Ig Fusion Protein in Chinese Hamster Ovary Cells by Dexamethasone", Biotechnology and Bioengineering, Oct. 15, 2010, vol. 107, No. 3, pp. 488-496.
Julenius, et al., "Prediction, conservation analysis, and structural characterization of mammalian mucin-type O-glycosylation sites", Glycobiology, 2004, vol. 15, No. 2, pp. 153-164.
Karin, et al., "Human metallothionein genes—primary structure of the metallothionein-II gene and a related processed gene", Nature, Oct. 28, 1982, vol. 299, pp. 797-802.
Kolhekar, et al., "Peptidylglycine α-Hydroxylating Monooxygenase: Active Site Residues, Disulfide, Linkages, and a Two-Domain Model of the Catalytic Core", Biochemistry, 1997, vol. 36, pp. 10901-10909.
Lis, et al., "Protein glycosylation Structural and functional aspects", Eur. J. Biochem., 1993, vol. 218, pp. 1-27.
Lowe, et al., "A Genetic Approach to Mammalian Glycan Function", Annu. Rev. Biochem., 2003, vol. 72, pp. 643-691.
Qian, et al., "Glucocorticoid Receptor-Mediated Reduction of IgG-Fusion Protein Aggregation in Chinese Hamster Ovary Cells", Biotechnol. Prog., 2010, vol. 26, No. 5, pp. 1417-1423.
Sambrook, et al., "Molecular Cloning a Laboratory Manual Second Edition", CSH 1989, 29 pgs.

(Continued)

Primary Examiner — Jessica H Roark
(74) Attorney, Agent, or Firm — Nickki L. Parlet (57) ABSTRACT The present invention provides methods for reducing glycoprotein aggregation by optimizing the number of O-linked glycosylation sites.

2 Claims, 6 Drawing Sheets (56) References Cited

OTHER PUBLICATIONS

Schwartz, et al., "Effects of Atorvastatin on Early Recurrent Ischemic Events in Acute Coronary Syndromes the MIRACL Study: A Randomized Controlled Trial", JAMA, Apr. 4, 2001, vol. 285, No. 13, pp. 1711-1719.
Shimatake, et al., "Purified λ regulatory protein cII positively activates promoters for lysogenic development", Nature, Jul. 9, 1981, vol. 292, pp. 128-132.
Stinchcomb, et al., "Isolation and characterisation of a yeast chromosomal replicator", Nature, Nov. 1, 1979, vol. 282, pp. 39-43.
Toyama, et al., "Human chorionic gonadotropin α and human cytomegalovirus promoters are extremely active in the fission yeast *Schizosaccharomyces pompe*", FEBS, Jul. 1990, vol. 268, No. 1, pp. 217-221.
Tschumper, et al., "Sequence of a yeast DNA fragment containing a chromosomal replicator and the TRP1 gene", Gene, 1980, vol. 10, pp. 157-166.
Urlaub, et al., "Effect of Gamma Rays at the Dihydrofolate Reductase Locus: Deletions and Inversions", Somatic Cell and Molecular Genetics, 1986, vol. 12, No. 6, pp. 555-566.
Van den Steen, et al., "Concepts and Principles of O-Linked Glycosylation", Critical Reviews in Biochemistry and Molecular Biology, 1998, vol. 33, No. 3, pp. 151-208.
Weenen, et al., "Long-Acting Follicle-Stimulating Hormone Analogs Containing N-Linked Glycosylation Exhibited Increased Bioactivity Compared with O-Linked Analogs in Female Rats", The Journal of Clinical Endocrinology & Metabolism, 2004, vol. 89, No. 10, pp. 5204-5212.

\* cited by examiner

```
ATGGGTGTACTGCTCACACAGAGGACGCTGCTCAGTCTGGTCCTTGCACTCCTGTTTCCA        -19
M---G---V---L---L---T---Q---R---T---L---L---S---L---V---L---A---L---L---F---P---   -7

AGCATGGCGAGCATGGCAATGCACGTGGCCCAGCCTGCTGTGGTACTGGCCAGCAGCCGA        +42
S---M---A---S---M---A---M---H---V---A---Q---P---A---V---V---L---A---S---S---R---   +14
                +1

GGCATCGCTAGCTTTGTGTGTGAGTATGCATCTCCAGGCAAATATACTGAGGTCCGGGTG       +102
G---I---A---S---F---V---C---E---Y---A---S---P---G---K---Y---T---E---V---R---V---  +34

ACAGTGCTTCGGCAGGCTGACAGCCAGGTGACTGAAGTCTGTGCGGCAACCTACATGATG       +162
T---V---L---R---Q---A---D---S---Q---V---T---E---V---C---A---A---T---Y---M---M---  +54

GGGAATGAGTTGACCTTCCTAGATGATTCCATCTGCACGGGCACCTCCAGTGGAAATCAA       +222
G---N---E---L---T---F---L---D---D---S---I---C---T---G---T---S---S---G---N---Q---  +74

GTGAACCTCACTATCCAAGGACTGAGGGCCATGGACACGGGACTCTACATCTGCAAGGTG       +282
V---N---L---T---I---Q---G---L---R---A---M---D---T---G---L---Y---I---C---K---V---  +94

GAGCTCATGTACCCACCGCCATACTACGAGGGCATAGGCAACGGAACCCAGATTTATGTA       +342
E---L---M---Y---P---P---P---Y---Y---E---G---I---G---N---G---T---Q---I---Y---V---  +114

ATTGATCCAGAACCGTGCCCAGATTCTGATCAGGAGCCCAAATCTTCTGACAAAACTCAC       +402
I---D---P---E---P---C---P---D---S---D---Q---E---P---K---S---S---D---K---T---H---  +134

ACATCCCCACCGTCCCCAGCACCTGAACTCCTGGGGGGATCGTCAGTGTTCCTCTTCCCC       +462
T---S---P---P---S---P---A---P---E---L---L---G---G---S---S---V---F---L---F---P---  +154

CCAAAACCCAAGGACACCCTCATGATCTCCCGGACCCCTGAGGTCACATGCGTGGTGGTG       +522
P---K---P---K---D---T---L---M---I---S---R---T---P---E---V---T---C---V---V---V---  +174

GACGTGAGCCACGAAGACCCTGAGGTCAAGTTCAACTGGTACGTGGACGGCGTGGAGGTG       +582
D---V---S---H---E---D---P---E---V---K---F---N---W---Y---V---D---G---V---E---V---  +194

CATAATGCCAAGACAAAGCCGCGGGAGGAGCAGTACAACAGCACGTACCGTGTGGTCAGC       +642
H---N---A---K---T---K---P---R---E---E---Q---Y---N---S---T---Y---R---V---V---S---  +214

GTCCTCACCGTCCTGCACCAGGACTGGCTGAATGGCAAGGAGTACAAGTGCAAGGTCTCC       +702
V---L---T---V---L---H---Q---D---W---L---N---G---K---E---Y---K---C---K---V---S---  +234

AACAAAGCCCTCCCAGCCCCCATCGAGAAAACCATCTCCAAAGCCAAAGGGCAGCCCCGA       +762
N---K---A---L---P---A---P---I---E---K---T---I---S---K---A---K---G---Q---P---R---  +254

GAACCACAGGTGTACACCCTGCCCCCATCCCGGGATGAGCTGACCAAGAACCAGGTCAGC       +822
E---P---Q---V---Y---T---L---P---P---S---R---D---E---L---T---K---N---Q---V---S---  +274

CTGACCTGCCTGGTCAAAGGCTTCTATCCCAGCGACATCGCCGTGGAGTGGGAGAGCAAT       +882
L---T---C---L---V---K---G---F---Y---P---S---D---I---A---V---E---W---E---S---N---  +294

GGGCAGCCGGAGAACAACTACAAGACCACGCCTCCCGTGCTGGACTCCGACGGCTCCTTC       +942
G---Q---P---E---N---N---Y---K---T---T---P---P---V---L---D---S---D---G---S---F---  +314

TTCCTCTACAGCAAGCTCACCGTGGACAAGAGCAGGTGGCAGCAGGGGAACGTCTTCTCA      +1002
F---L---Y---S---K---L---T---V---D---K---S---R---W---Q---Q---G---N---V---F---S---  +334

TGCTCCGTGATGCATGAGGCTCTGCACAACCACTACACGCAGAAGAGCCTCTCCCTGTCT      +1062
C---S---V---M---H---E---A---L---H---N---H---Y---T---Q---K---S---L---S---L---S---  +354

CCGGGTAAATGA
P---G---K---*
```

METHODS FOR REDUCING GLYCOPROTEIN AGGREGATION

Throughout this application various publications are referenced. The disclosures of these publications in their entireties are hereby incorporated by reference into this application in order to more fully describe the state of the art to which this invention pertains.

FIELD OF THE INVENTION

This invention relates to methods for reducing glycoprotein aggregation by optimizing the number of O-linked glycosylation sites.

BACKGROUND OF THE INVENTION

Protein glycosylation is a critical quality attribute in determining the potency and pharmacokinetic longevity of a biologic. Understanding how each glycosylation site affects the overall function of the protein helps optimize final product quality. By achieving a homogeneous glycosylation profile, increases in yield can be achieved with assurance of product comparability.

O-linked glycosylation refers to the attachment of one of the sugars N-acetylgalactosamine, galactose, or xylose to a hydroxyamino acid, most commonly serine or threonine. O-linked sugar residues have fewer structural rules than N-linked glycosylation and therefore create a greater diversity in glycoforms. O-linked glycosylation is difficult to predict due to lack of consensus recognition sequences. However, neural network approaches have been developed to better predict mucin-type O-linked sites (Julenius, K., et.al. 2005. *Glycobiology* 15, 153-164). While most reports to date document the role of O-glycans in the glycoproteins' binding capability or the masking of its peptide backbone, one particular case study demonstrates that follicle-stimulating hormone (FSH) analogs with more O-linked sites are less bioactive than FSH analogs with increased N-linked glycosylation sites (Weenen, C. et al. 2004. *J Clin Endocrinol Metab* 89, 5204-5212). O-linked glycans have been shown to be non-essential for cell surface expression of glycoprotein gC-1 but may interfere with its epitope's binding domain and its binding capability (Biller, M. et al. 2000. *Glycobiology* 10, 1259-1269).

The presence of glycosylation is believed to affect immunogenicity, efficacy, solubility, and half-life of commercial biologics (Lis, H. et.al. 1993. *Eur J Biochem* 218, 1-27; Lowe, J. B. et.al. 2003. *Annu Rev Biochem* 72, 643-691; Van den Steen, P. et.al. 1998. *Grit Rev Biochem Mol Biol* 33, 151-208). However, most literature focuses on the effects of N-linked glycosylation (Hossler, P. et.al. 2009. *Glycobiology* 19, 936-949). The information regarding the effects of O-linked glycosylation on protein quality is scarce; especially with respect to protein aggregation.

Aggregation of a protein therapeutic during manufacture is undesirable and requires extensive downstream processing for its removal. Therefore, there is a need to minimize protein aggregation resulting in reduced manufacturing costs and accelerated process optimization. The discovery of the relationship between O-linked glycosylation and aggregation of a therapeutic glycoprotein enables the manufacturer to modify the therapeutic glycoprotein early in product development.

SUMMARY OF INVENTION

This invention provides methods for reducing glycoprotein aggregation by optimizing the number of O-linked glycosylation sites. The glycoprotein may be a fusion protein. The fusion protein may comprise the hinge portion of the Fc region of a human immunoglobulin. The human immunoglobulin may be human IgG.

The invention provides a method of reducing glycoprotein aggregation comprising elimination of one or more O-linked glycosylation sites therein. The O-linked glycosylaiton site to be eliminated may be in the hinge region of a Fc domain.

The invention provides a method of reducing glycoprotein aggregation comprising elimination of one or more O-linked glycosylation sites through amino acid substitution and/or deletion. The one or more substituted and/or deleted O-linked glycosylaiton sites may be in the hinge region of a Fc domain shown in SEQ ID NO:5. The O-linked glycosylation sites in the hinge region of the Fc domain shown in SEQ ID NO:5 that may be eliminated are selected from S248, T252, T254. The one or more substituted and/or deleted O-linked glycosylaiton sites may be in the hinge region of the mutated Fc domain shown in SEQ ID NO:4. The O-linked glycosylation sites in the hinge region of the Fc domain shown in SEQ ID NO:4 that may be eliminated are selected from S129, S130, S136, S139, T133, T135.

The invention provides the CTLA4Ig fusion glycoprotein shown in FIG. 6 comprising elimination of at least one of the O-linked glycosylation sites selected from S129, S130, S136, S139, T133, T135.

BRIEF DESCRIPTION OF THE FIGURES

FIG. 6 depicts a nucleotide and amino acid sequence of belatacept, a cytotoxic T-lymphocyte antigen 4 (CTLA4) fusion protein comprising a signal peptide (alanine at position −1 to methionine at positon −26); a mutated extracellular domain of CTLA4 starting at methionine at position +1 and ending at aspartic acid at position +124, or starting at alanine at position −1 and ending at aspartic acid at position +124; a glutamic acid linker at position +125; and the hinge-CH2-CH3 domains of the Fc domain of a human immunoglobulin G1 antibody at position +126 to +357. The sequence described in FIG. 6 corresponds to SEQ ID NOS: 1 and 2, which depict a nucleotide and amino acid sequence, respectively, of belatacept, a CTLA4 fusion protein, comprising a 26 amino acid signal peptide; a mutated extracellular domain of CTLA4 starting at methionine at position +27 and ending at aspartic acid at position +150, or starting at alanine at position +26 and ending at aspartic acid at position +150; a glutamic acid linker at position +151; and the hinge-CH2-CH3 domains of the Fc domain of a human immunoglobulin G1 antibody at position +152 to +383.

DETAILED DESCRIPTION OF THE INVENTION

All scientific and technical terms used in this application have meanings commonly used in the art unless otherwise specified. As used in this application, the following words or phrases have the meanings specified.

As used herein, "belatacept" is a fusion protein that is a soluble CTLA4Ig mutant molecule comprising an extracellular domain of wildtype CTLA4 with amino acid changes A29Y (a tyrosine amino acid residue substituting for an alanine at position 29) and L104E (a glutamic acid amino acid residue substituting for a leucine at position +104), joined to an Ig tail (included in FIG. 6, SEQ ID NOS: 1 and 2; DNA encoding L104EA29Y-Ig was deposited on Jun. 20, 2000, with the American Type Culture Collection (ATCC) under the provisions of the Budapest Treaty. It has been accorded ATCC accession number PTA-2104. L104EA29Y-Ig is further described in U.S. Pat. No. 7,094,874, issued on Aug. 22, 2006, which is incorporated by reference herein in their entireties.

As used herein, "aggregate" is used interchangeably with "high molecular weight species". For example, a high molecular weight aggregate may be a tetramer, a pentamer or a hexamer.

The monomer, dimer and HMW species of a glycoprotein may be separated by size exclusion chromatography (SEC). SEC separates molecules based on the molecular size. Separation is achieved by the differential molecular exclusion or inclusion as the molecules migrate along the length of the column. Thus, resolution increases as a function of column length. For example, CTLA4Ig molecule samples may be separated using a 2695 Alliance HPLC (Waters, Milford, Mass.) equipped with TSK Gel® G3000SWXL (300 mm×7.8 mm) and TSK Gel® G3000SWXL (40 mm×6.0 mm) columns (Tosoh Bioscience, Montgomery, Pa.) in tandem. Samples at 10 mg/ml (20 µl aliquot) are separated using a mobile phase consisting of 0.2 M $KH_2PO_4$, 0.9% NaCl, pH 6.8, at a flow rate of 1.0 ml/min. Samples are monitored at an absorbance of 280 nm using Water's 2487 Dual Wavelength detector. Using this system, the HMW species has a retention time of 7.5 min ±1.0 min. Each peak is integrated for area under the peak. The % HMW species calculated by dividing the HMW peak area by the total peak area.

As used herein, the terms "optimizing," "eliminating," "elimination" and "eliminated" are used interchangeably with the terms "substituted" and/or "deleted".

As used herein, the "hinge region" of a human immunoglobulin antibody joins the Fab arms to the Fc piece. The flexibility of the hinge region allows the Fab arms to adopt a wide range of angles, permitting binding to epitopes spaced variable distances apart.

The hinge region of human IgG immunoglobulin comprises the amino acid sequence:

245
(SEQ ID NO: 5)
EPKSCDKTHTCPPCPAPELLGGPSVFLF 272

The hinge region of belatacept comprises the amino acid sequence starting with glutamic acid at position +152 and ending at phenylalanine at position +179 as shown in SEQ ID NO: 2.

This invention relates to methods for reducing glycoprotein aggregation by optimizing the number of O-linked glycosylation sites therein. The glycoprotein may be a fusion protein. The fusion protein may comprise the hinge portion of an Fc region of a human immunoglobulin. The human immunoglobulin may be human IgG.

In one aspect, the invention provides a method for reducing glycoprotein aggregation comprising elimination of one or more of O-linked glycosylation sites within the hinge region of the Fc domain.

In another aspect, the invention provides a method for reducing glycoprotein aggregation comprising substituting and/or deleting at least one of the O-linked glycosylation sites within the hinge region of the Fc domain, wherein the O-linked glycosylation site is selected from S248, T252, T254 shown in SEQ ID NO: 5. The amount of high molecular weight species (HMW) is an important quality control parameter in biologics manufacturing, and HMW formation is an undesirable side effect in protein therapeutic expression systems. HMW species are formed covalently or non-covalently and considered to be protein aggregates.

Figure 1:
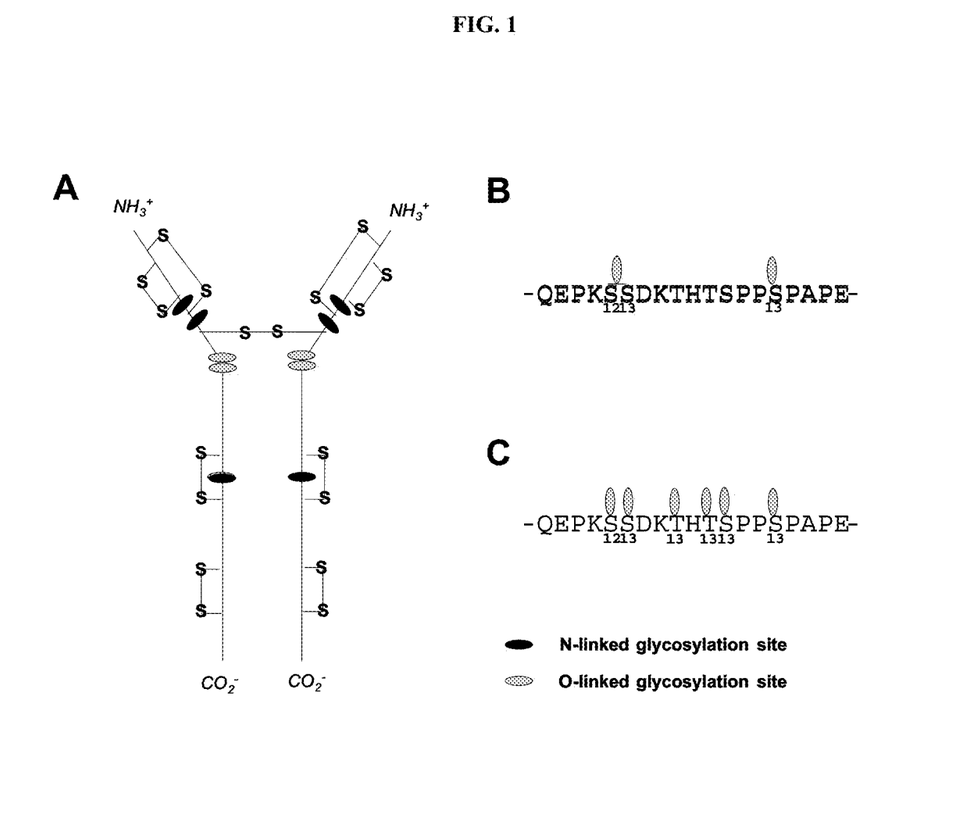
FIG. 1A-1C show the glycosylation sites in belatacept. A shows N-linked glycosylation and O-linked glycosylation sites, deduced from the published data (AMA 2008; Schwartz et al. 2001). B shows O-linked glycosylation sites, mapped by mass spectrometric analysis on tryptic peptide fragments(SEQ ID NO:3). One O-linked site could not be definitively assigned to S129 or S130. C shows the O-linked glycosylation sites predicted by the neural network method NetOGlyc3.1(SEQ ID NO: 4). The belatacept amino acid sequence shown in FIG. 6 was used as input into the NetOGlyc3.1 software online at www.cbs.dtu.dk/services/netoglyc.

In order to better understand the effects of O-linked glycosylation of protein therapeutics, a highly glycosylated model was chosen for investigation-belatacept (Nulojix®), a fusion protein CTLA4-Ig. The known N-linked and O-linked glycosylation sites for belatacept are shown in FIG. 1A Amino acid sequencing and peptide mapping have confirmed there are three N-linked and two dominant O-linked glycosylation sites on belatacept and abatacept (FIG. 1B), but the neural network method NetOGlyc3.1 predicted that there were six O-linked sites clustered between S129 and S139 (FIG. 1C). This discrepancy reflects the O-linked glycan heterogeneity with respect to variable site occupancy (macroheterogeneity).

As shown in Example 1 protein aggregation was reduced by eliminating O-linked sites through substitution or deletion judged by a significant reduction in the amount of HMW species in the protein products. Protein aggregation is reduced by 5% to 98%, from 8% to 60%, from 8% to 30 by elimination of at least one or more O-linked glycosylation sites.

In one aspect, the invention provides a method for reducing glycoprotein aggregation comprises substitution and/or deletion of at least one of the O-linked glycosylation sites within the hinge region shown in SEQ ID NO: 4.

In another aspect, the invention provides a method for reducing glycoprotein aggregation comprises substitution and/or deletion of at least one of the O-linked glycosylation sites, selected from S129, S130, S136, S139, T133, T135 shown in SEQ ID NO: 4.

In another aspect, the invention provides a method for reducing glycoprotein aggregation comprising substitution and/or deletion of O-linked glycosylation sites S129 and/or S139 shown in SEQ ID NO: 4.

In Example 1, site-directed mutagenesis was carried out with either a complete deletion or substitution with alanine or glutamine. Typically, residues that protrude out of the surface of the molecule are substituted with alanine and the buried residues are substituted with glutamine to avoid structural collapse. With respect to creating a functional protein, the only difference between an alanine and a serine is the substitution of hydrogen with a hydroxyl, which is unlikely to modify the general structure of the protein. In this model protein, even a complete deletion of the amino acid still resulted in secretion of a properly folded protein.

In another aspect, the invention provides the fusion protein shown in FIG. 6 comprising deletion of O-linked glycosylation site S129 or S139.

In another aspect, the invention provides the fusion protein shown in FIG. 6 comprising deletion of O-linked glycosylation site S129 and S139.

In another aspect, the invention provides the fusion protein shown in FIG. 6 comprising substitution of S129 with glutamine (Q) or alanine (A).

In another aspect, the invention provides the fusion protein shown in FIG. 6 comprising substitution of S139 with glutamine (Q) or alanine (A).

In another aspect, the invention provides the fusion protein shown in FIG. 6 comprising A130A133A135A136A139 substitutions.

In another aspect, the invention provides the fusion protein shown in FIG. 6 comprising A129A133A135A136A139 substitutions.

In another aspect, the invention provides the fusion protein shown in FIG. 6 comprising deletion of amino acids S129S130S139.

In another aspect, the invention provides the fusion protein shown in FIG. 6 comprising substitution of one or more of S130, T133, T135 and S136 with alanine (A).

Methods for Producing the CTLA4Ig Molecules of the Invention Expression of CTLA4Ig molecules can be in prokaryotic cells. Prokaryotes most frequently are represented by various strains of bacteria. The bacteria may be a gram positive or a gram negative. Typically, gram-negative bacteria such as *E. coli* are preferred. Other microbial strains may also be used.

Sequences, described above, encoding CTLA4Ig molecules can be inserted into a vector designed for expressing foreign sequences in prokaryotic cells such as *E. coli*. These vectors can include commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al., (1977) Nature 198:1056), the tryptophan (trp) promoter system (Goeddel, et al., (1980) Nucleic Acids Res. 8:4057) and the lambda derived $P_L$ promoter and N-gene ribosome binding site (Shimatake, et al., (1981) Nature 292:128).

Such expression vectors will also include origins of replication and selectable markers, such as a beta-lactamase or neomycin phosphotransferase gene conferring resistance to antibiotics, so that the vectors can replicate in bacteria and cells carrying the plasmids can be selected for when grown in the presence of antibiotics, such as ampicillin or kanamycin.

The expression plasmid can be introduced into prokaryotic cells via a variety of standard methods, including but not limited to $CaCl_2$-shock (Cohen, (1972) Proc. Natl. Acad. Sci. USA 69:2110, and Sambrook et al. (eds.), "Molecular Cloning: A Laboratory Manual", 2nd Edition, Cold Spring Harbor Press, (1989)) and electroporation.

In accordance with the practice of the invention, eukaryotic cells are also suitable host cells. Examples of eukaryotic cells include any animal cell, whether primary or immortalized, yeast (e.g., *Saccharomyces cerevisiae, Schizosaccharomyces pombe*, and *Pichia pastoris*), and plant cells. Myeloma, COS and CHO cells are examples of animal cells that may be used as hosts. Particular CHO cells include, but are not limited to, DG44 (Chasin, et la., 1986 Som. Cell. Molec. Genet. 12:555-556; Kolkekar 1997 Biochemistry 36:10901-10909), CHO-K1 (ATCC No. CCL-61), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), and RR-CHOK1 designated ECACC 92052129 (CAMR, Salisbury, Wiltshire, UK). Illustrative plant cells include tobacco (whole plants, cell culture, or callus), corn, soybean, and rice cells. Corn, soybean, and rice seeds are also acceptable.

Nucleic acid sequences encoding CTLA4Ig molecules described above can also be inserted into a vector designed for expressing foreign sequences in a eukaryotic host. The regulatory elements of the vector can vary according to the particular eukaryotic host.

Commonly used eukaryotic control sequences for use in expression vectors include promoters and control sequences compatible with mammalian cells such as, for example, CMV promoter (CDM8 vector) and avian sarcoma virus (ASV) (πLN vector). Other commonly used promoters include the early and late promoters from Simian Virus 40 (SV40) (Fiers, et al., (1973) Nature 273:113), or other viral promoters such as those derived from polyoma, Adenovirus 2, and bovine papilloma virus. An inducible promoter, such as hMTII (Karin, et al., (1982) Nature 299:797-802) may also be used.

Vectors for expressing CTLA4Ig molecules in eukaryotes may also carry sequences called enhancer regions. These are important in optimizing gene expression and are found either upstream or downstream of the promoter region.

Examples of expression vectors for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSGS vectors (Stratagene)), retroviral vectors (e.g., pFB vectors (Stratagene)), pCDNA-3 (Invitrogen) or modified forms thereof,adenoviral vectors; Adeno-associated virus vectors, baculovirus vectors, yeast vectors (e.g., pESC vectors (Stratagene)).

Nucleic acid sequences encodingCTLA4Ig molecules can integrate into the genome of the eukaryotic host cell and replicate as the host genome replicates. Alternatively, the vector carrying CTLA4Ig molecules can contain origins of replication allowing for extrachromosomal replication.

For expressing the nucleic acid sequences in *Saccharomyces cerevisiae*, the origin of replication from the endogenous yeast plasmid, the 2μ circle can be used. (Broach, (1983) Meth. Enz. 101:307). Alternatively, sequences from the yeast genome capable of promoting autonomous replication can be used (see, for example, Stinchcomb et al., (1979) Nature 282:39); Tschemper et al., (1980) Gene 10:157; and Clarke et al., (1983) Meth. Enz. 101:300).

Transcriptional control sequences for yeast vectors include promoters for the synthesis of glycolytic enzymes (Hess et al., (1968) J. Adv. Enzyme Reg. 7:149; Holland et al., (1978) Biochemistry 17:4900). Additional promoters known in the art include the CMV promoter provided in the CDM8 vector (Toyama and Okayama, (1990) FEBS 268: 217-221); the promoter for 3-phosphoglycerate kinase (Hitzeman et al., (1980) J. Biol. Chem. 255:2073), and those for other glycolytic enzymes.

Other promoters are inducible because they can be regulated by environmental stimuli or the growth medium of the cells. These inducible promoters include those from the genes for heat shock proteins, alcohol dehydrogenase 2, isocytochrome C, acid phosphatase, enzymes associated with nitrogen catabolism, and enzymes responsible for maltose and galactose utilization.

Regulatory sequences may also be placed at the 3' end of the coding sequences. These sequences may act to stabilize messenger RNA. Such terminators are found in the 3' untranslated region following the coding sequences in several yeast-derived and mammalian genes.

Illustrative vectors for plants and plant cells include, but are not limited to, *Agrobacterium* $T_i$ plasmids, cauliflower mosaic virus (CaMV), and tomato golden mosaic virus (TGMV).

Mammalian cells can be transformed by methods including but not limited to, transfection in the presence of calcium phosphate, microinjection, electroporation, or via transduction with viral vectors.

Methods for introducing foreign DNA sequences into plant and yeast genomes include (1) mechanical methods, such as microinjection of DNA into single cells or protoplasts, vortexing cells with glass beads in the presence of DNA, or shooting DNA-coated tungsten or gold spheres into cells or protoplasts; (2) introducing DNA by making cell membranes permeable to macromolecules through polyethylene glycol treatment or subjection to high voltage electrical pulses (electroporation); or (3) the use of liposomes (containing cDNA) which fuse to cell membranes.

U.S. Pat. No. 7,541,164 and U.S. Pat. No. 7,332,303 teach processes for the production of proteins of the invention, specifically recombinant glycoprotein products, by animal or mammalian cell cultures and are herein incorporated by reference.

Following the protein production phase of the cell culture process, CTLA4Ig molecules are recovered from the cell culture medium using techniques understood by one skilled in the art. In particular, the CTLA4Ig molecule is recovered from the culture medium as a secreted polypeptide.

The culture medium is initially centrifuged to remove cellular debris and particulates. The desired protein subsequently is purified from contaminant DNA, soluble proteins, and polypeptides, with the following non-limiting purification procedures well-established in the art: SDS-PAGE; ammonium sulfate precipitation; ethanol precipitation; fractionation on immunoaffinity or ion-exchange columns; reverse phase HPLC; chromatography on silica or on an anion-exchange resin such as QAE or DEAE; chromatofocusing; gel filtration using, for example, Sephadex G-75™ column; and protein A Sepharose™ columns to remove contaminants such as IgG. Addition of a protease inhibitor, such as phenyl methyl sulfonyl fluoride (PMSF), or a protease inhibitor cocktail mix also can be useful to inhibit proteolytic degradation during purification. A person skilled in the art will recognize that purification methods suitable for a protein of interest, for example a glycoprotein, can require alterations to account for changes in the character of the protein upon expression in recombinant cell culture.

Purification techniques and methods that select for the carbohydrate groups of the glycoprotein are also of utility within the context of the present invention. For example, such techniques include, HPLC or ion-exchange chromatography using cation- or anion-exchange resins, wherein the more basic or more acidic fraction is collected, depending on which carbohydrate is being selected for. Use of such techniques also can result in the concomitant removal of contaminants.

The purification method can further comprise additional steps that inactivate and/or remove viruses and/or retroviruses that might potentially be present in the cell culture medium of mammalian cell lines. A significant number of viral clearance steps are available, including but not limited to, treating with chaotropes such as urea or guanidine, detergents, additional ultrafiltration/diafiltration steps, conventional separation, such as ion-exchange or size exclusion chromatography, pH extremes, heat, proteases, organic solvents or any combination thereof.

The purified CTLA4Ig molecule require concentration and a buffer exchange prior to storage or further processing. A Pall Filtron TFF system may be used to concentrate and exchange the elution buffer from the previous purification column with the final buffer desired for the drug substance.

In one aspect, purified CTLA4Ig molecules, which have been concentrated and subjected to diafiltration step, can be filled into 2-L Biotainer® bottles, 50-L bioprocess bag or any other suitable vessel. CTLA4Ig molecules in such vessels can be stored for about 60 days at 2° to 8° C. prior to freezing. Extended storage of purified CTLA4Ig molecules at 2° to 8° C. may lead to an increase in the proportion of HMW species. Therefore, for long-term storage, CTLA4Ig molecules can be frozen at about −70° C. prior to storage and stored at a temperate of about −40° C. The freezing temperature can vary from about −50° C. to about −90° C. The freezing time can vary and largely depends on the volume of the vessel that contains CTLA4Ig molecules, and the number of vessels that are loaded in the freezer. For example, in one embodiment, CTLA4Ig molecules are in 2-L Biotainer® bottles. Loading of less than four 2-L Biotainer® bottles in the freezer may require from about 14 to at least 18 hours of freezing time. Loading of at least four bottles may require from about 18 to at least 24 hours of freezing time. Vessels with frozen CTLA4Ig molecules are stored at a temperature from about −35° C. to about −55° C. The storage time at a temperature of about −35° C. to about −55° C. can vary and can be as short as 18 hours. The frozen drug substance can be thawed in a control manner for formulation of drug product.

Co-pending US patent application Publication No.: US20090252749, and US20100166774A1 filed on Dec. 19, 2006 teach processes for the production of proteins of the invention, specifically recombinant glycoprotein products, by animal or mammalian cell cultures and is herein incorporated by reference.

EXAMPLE 1

The purpose of this study was to understand the phenomenon of macroheterogeneity with a goal to design glycoproteins with more homogeneous glycans by site-directed mutagenesis of O-linked sites and define the relationship between O-linked sites and aggregation.

Materials and Methods

Cell Lines and Culture Condition

Human embryonic kidney 293-F (HEK293-F) FreeStyle (Invitrogen) suspension cells were grown in serum-free FreeStyle 293 expression medium (Invitrogen) and passaged in shake flasks every three days. Cells were incubated at 130 rpm on an orbital shaker platform in a 37° C. incubator with 6% $CO_2$ in air.

Computational Predictions of O-Linked Glycosylation Sites

The O-linked glycosylation sites of belatacept were predicted by the neural network method NetOGlyc3.1 at www.cbs.dtu.dk/services/netoglyc. The result for belatacept wild-type is shown in FIG. 1C. The belatacept amino acid sequence was used as input into the NetOGlyc3.1 software online. The output predicted that belatacept contains six O-linked sites at S129, S130, T133, T135, S136, and S139.

Construction of Fusion Protein Mutants

Site-directed mutagenesis was carried out with either a complete deletion or substitution with alanine or glutamine. The mutagenesis reaction was performed with methylated belatacept plasmid DNA as the template, and with two overlapping primers, one of which contained the target mutation. The mutagenesis products were transformed into *E. coli* competent cells, where unmethylated linear mutated DNA was circularized and replicated. Plasmid DNAs were purified with a Maxi-prep plasmid kit (Qiagen, Mississauga, ON, Canada) and sequenced to confirm the correct mutant was present (Cogenics, Houston, Tex.).

Transient Expression of Belatacept and its Variants in HEK-293F Suspension Cells One day prior to transfection, cells were seeded at 0.6 million cells/ml and agitated on an orbital shaker platform rotating at 135 rpm at 37° C. with 6% $CO_2$. On the day of transfection, cells were diluted to 1.0 million cells/ml and added into a 125-ml shake flask at 30 ml culture volume. Forty micrograms of plasmid DNA were diluted into OptiPro SFM (Invitrogen) to a total volume of 0.6 ml and mixed. In a separate tube, 40 μl of FreeStyle MAX Reagent (Invitrogen) was also diluted with Opti-Pro SFM to a total volume of 0.6 ml. Diluted DNA solution and diluted transfection reagent were mixed gently and incubated at room temperature for 20 minutes. DNA-transfection-reagent mixture was then slowly added to freshly diluted cells in 125-ml flasks. Transfected cells were incubated at 37° C., 6% $CO_2$ on an orbital shaker platform rotating at 135 rpm for 7 days in batch mode.

Determination of Belatacept Mutant Concentration and Purification

Samples were centrifuged at 1000 rpm for ten minutes and the supernatants were stored at −20° C. before product titer assay. Fusion protein concentration was measured on an Octet QK (ForteBio, Menlo Park, Calif.), according to the manufacturer's instructions. The harvest samples were purified with Protein-A spin columns (Sartorius) for a final concentration of 0.2-0.3 mg/mL.

Determination of Total Sialylation and N-linked Sialylation

Protein-A purified samples were treated with PNGase and the asialylated and sialylated N-linked glycans were labeled with 2-AB (aminobenzamide). The 2-AB labeled oligosaccharides were separated into neutral and acidic fractions using a weak anion exchange HPLC method using a Glyko-GlycoSep C Column (7.5×75 mm, Prozyme, San Leandro, Calif.). The mobile phase consisted of a gradient, formed from a solution of 0.5 M ammonium formate, adjusted to pH 4.5 and a solution of 20% (v/v) acetonitrile in water. The flow rate was 0.75 mL/min and fluorescence detection was carried out using an excitation wavelength of 330 nm and an emission wavelength of 420 nm. N-linked sialic acid was calculated based on the fractions of asialylated and sialylated glycoforms.

Total sialic acid content was determined by the method described previously (Jing, Y., et.al. 2010. *Biotechnol Bioeng* 107, 488-496). Sialic acids (N-acetylneuraminic acid and N-glycolylneuraminic acid) from N- and O-linked glycosylation were released by partial acid hydrolysis and then separated by reversed-phase HPLC. N-glycolylneuraminic acid was below the limit of detection in all cases (<0.1 mol per mol glycoprotein).

The supernatant samples were purified with Protein-A capture and sialic acids including N-Acetylneuraminic (Neu5Ac) and N-Glycolylneuraminic acid (Neu5Gc) were released by partial acid hydrolysis and were separated by reversed-phase HPLC to determine total sialic acid content, which were derived from both N-linked and O-linked glycosylation.

Determination of Binding Kinetics

Kinetics of the binding of each mutant and wild-type to CD80-Ig was determined by immobilizing the CD80-Ig on the BIAcore sensor chip surface at densities of 200 RUs. Concentrations in the range of 10-200 nM in HBS-EP buffer (10 mM Hepes, 150 mM NaCl, 3 mM EDTA, 0.005% Tween-20) (pH 7.4) were injected over the sensor chip surface at a flow rate of 30 μL/min. Association and dissociation data were collected for 3 and 5 minutes, respectively at the different concentrations.

Determination of O-linked Glycoforms

Protein-A purified samples were diluted in 100 mM Tris, 25 mM NaCl, pH 7.6 and incubated with PNGase F overnight to remove N-linked oligosaccharides. Samples were then spiked with an internal standard of insulin, loaded onto a Waters Oasis HLB cartridge, and washed with 0.1 formic acid in 5% acetonitrile followed by gradient elution with 0.1 formic acid in acetonitrile. The capillary and cone voltages were 3 kV and 30 V, respectively, and scans made from 800 to 2500 m/z. Spectra were deconvoluted by MaxEnt1 algorithm to determine molecular masses and O-linked glycan species.

Size Exclusion Chromatography (SEC)

SEC was used to identify high molecular weight (HMW) species in wild-type and mutant belatacept samples by the method described previously (Qian, Y., et.al. 2010 *Biotechnol Prog* 26, 1417-1423). Protein-A purified samples and reference standard were directly injected into an HPLC equipped with a 7.8×300 mm Toso Haas Biosep TSK G3000SWXL column. The separation was isocratic using PBS at pH 7.2 at room temperature at a flow rate of 0.5 mL/minute for 30 minutes. The isocratic elution profile was monitored at 280 nm. Quantitation was performed by calculating relative peak area percentages of HMW, monomer and low molecular weight (LMW) species between the void and the inclusion volumes.

Results

Protein Expression, Sialylation and Binding Kinetics

Both wild type belatacept and its mutants were robustly expressed in HEK transient expression system, with all of the mutants secreting protein titer ranging from 100 to 150 mg/L; in particular, the successful synthesis and secretion of the mutants in which all six putative O-linked sites were eliminated indicates that O-linked glycosylation is not essential for belatacept synthesis.

Figure 2:
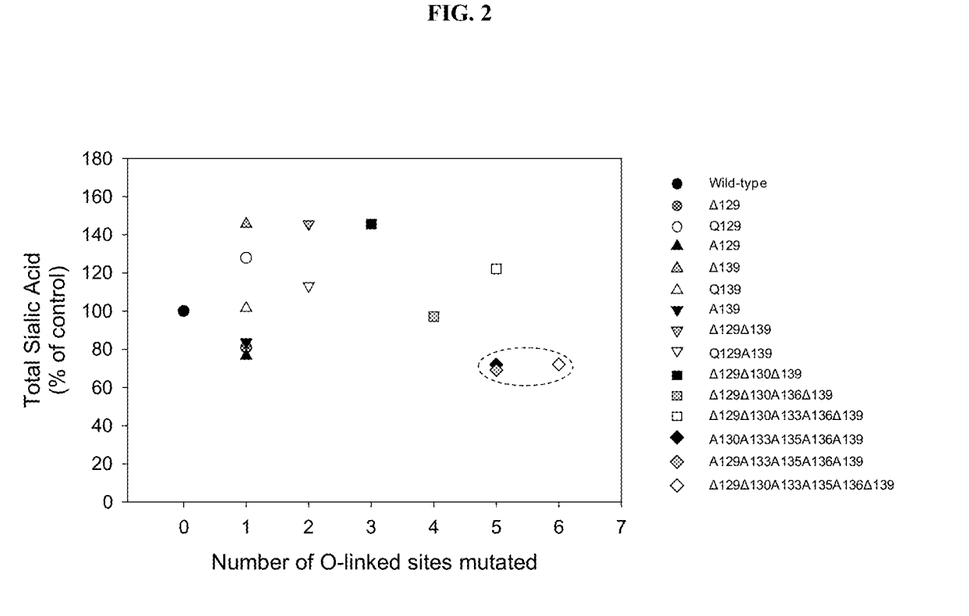
FIG. 2 shows that there is no correlation between the number of putative O-linked sites and total sialic acid content. The consistent total sialylation was detected when there was no O-linked glycosylation in three mutants (circled by a dot line).

Surprisingly there was no clear correlation between total sialylation and the number of available O-linked sites (FIG. 2). For example, the mutant with deletion of major O-linked sites (Δ129Δ139 or Δ129Δ130Δ139) had significant higher levels of total sialic acids than the wild-type; even when five O-linked sites were eliminated, the higher sialylation could still be seen in one mutant (Δ129Δ130A133A136Δ139). Three mutants showing the lowest total sialic acid contents were A130A133A135A136A139, A129A133A135A136A139 and Δ129Δ130A133A135A136Δ139.

Since no O-linked sialylation was detected in these three mutants (see the next section), the total sialic acid was considered to contain only N-linked sialic acid.

To ensure the functionality, the binding kinetics for each mutant was measured with CD80Ig and found to be comparable to the wild-type, and reference standards. Removing single and multiple O-linked sites had no significant effect on the CD80 binding kinetics in terms of the equilibrium constants and binding efficiency.

O-Linked Glycoforms

Glycosylation at Hidden O-Linked Sites

Figure 3:
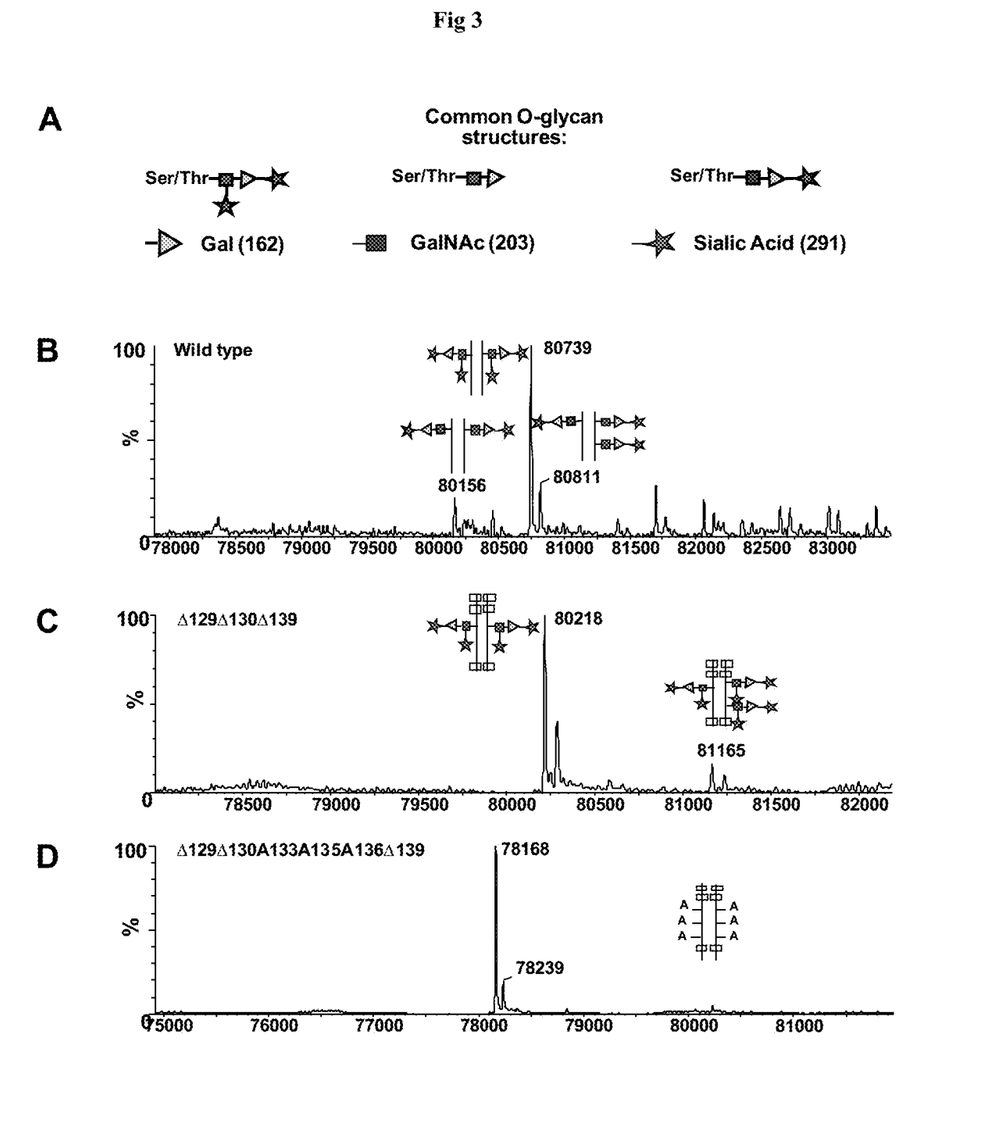
FIG. 3A-3D identify the O-linked glycosylation at hidden sites. A is a diagram illustrating common O-glycan structures. The number in parenthesis is molecular weight. Gal—galactose; GalNAc—N-acetylgalactosamine B is a deconvoluted mass spectra showing O-linked glycosylation in wild-type belatacept. C is a deconvoluted mass spectra showing O-linked glycosylation in the mutant that did not have S129, S130 and S139. O-linked glycosylation at T133, T135 and S136 was more detectable in the mutant after triple deletion at S129, S130 and S139. D is a deconvoluted mass spectra showing no O-linked glycosylation in the mutant that did not have S129, S130 and S139 and in which T133, T135 and S136 were substituted with alanine.

As shown in FIGS. 1B and 1C, peptide mapping only identified two major O-linked sites while there are six sites predicted by the computational O-glycosylation neural network method. To reveal potential hidden O-linked glycosylation sites, the known sites were disrupted by deleting S129, S130 and S139. Interestingly, O-linked glycosylation analysis did demonstrate existence of additional O-linked sites (FIG. 3C). This was further confirmed when belatacept was designed with additional mutations at positions 133, 135 and 136; while this mutant could be synthesized, secreted and bound to CD80, it did not produce any O-linked glycosylation (FIG. 3D).

Effect of Neighbor Sequence on the Formation of Variable O-Glycoforms

Figure 4:
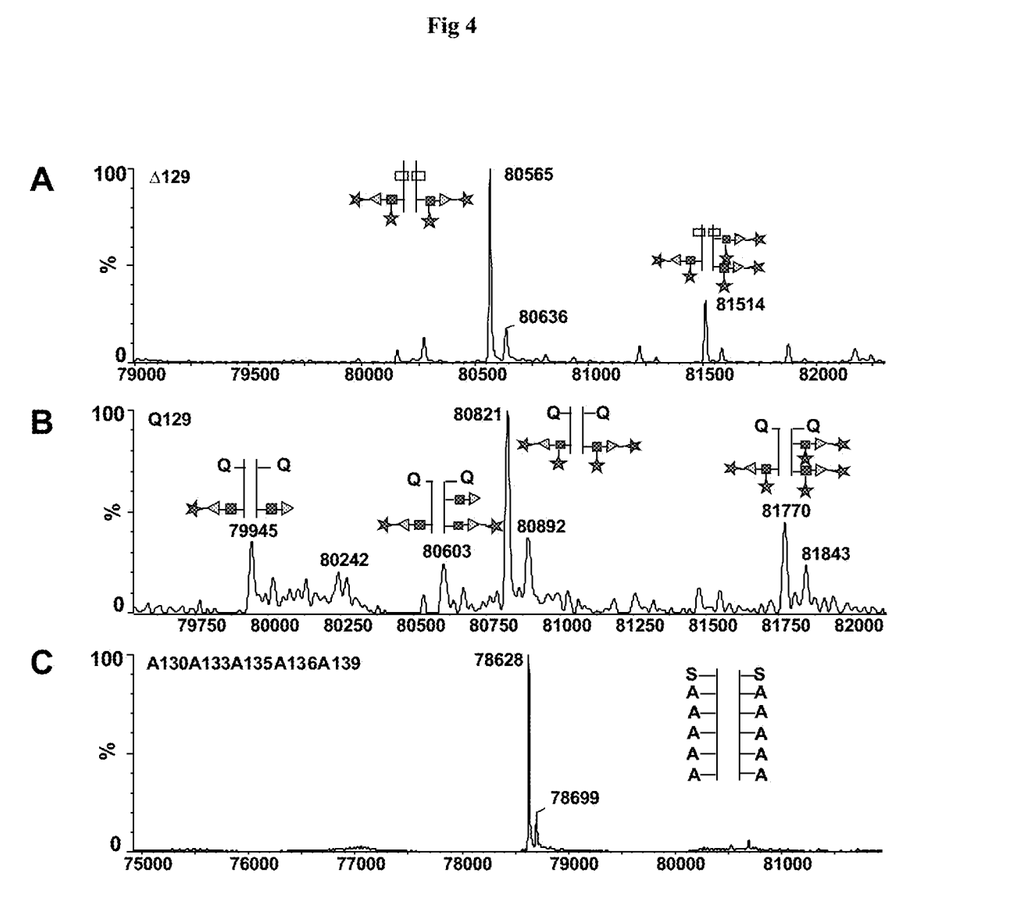
FIG. 4A-4C shows the formation of variable O-glycoforms by single mutation at the same site. A is a deconvoluted mass spectra showing O-linked glycosylation in the mutant with S129 deletion. B is a deconvoluted mass spectra showing O-linked glycosylation in the mutant with glutamine substitution at position 129. C is a deconvoluted mass spectra showing no O-linked glycosylation in the mutant with S129 intact and alanine substitution at position 130, 133, 135, 136 and 139.

FIG. 2 demonstrated that a single mutation at the same position caused a significant variation in total sialic acid contents. To pinpoint the source of the variation, those mutants were further analyzed for O-glycoforms. All mutants' O-linked glycosylation was found to be altered compared with the wild-type, and more interestingly O-linked glycosylation patterns of these mutants were different from each other (FIG. 4). By substituting with glutamine instead of alanine, multiple glycoforms were generated that were not previously seen in the wild-type protein, whereas the substitution of alanine narrowed the number of glycoforms. This indicates that O-glycosylation can be affected by its neighbor sequence, depending upon which amino acid is the placeholder. Furthermore, when S129 or S130 was left intact and the remainder five putative O-linked sites were removed by substituting with alanine at each site, no O-linked glycosylation could be formed (FIG. 4C), supporting the importance of microenvironment in the formation of O-glycoforms even though there are no consensus recognition sequences.

HMW Species

Figure 5:
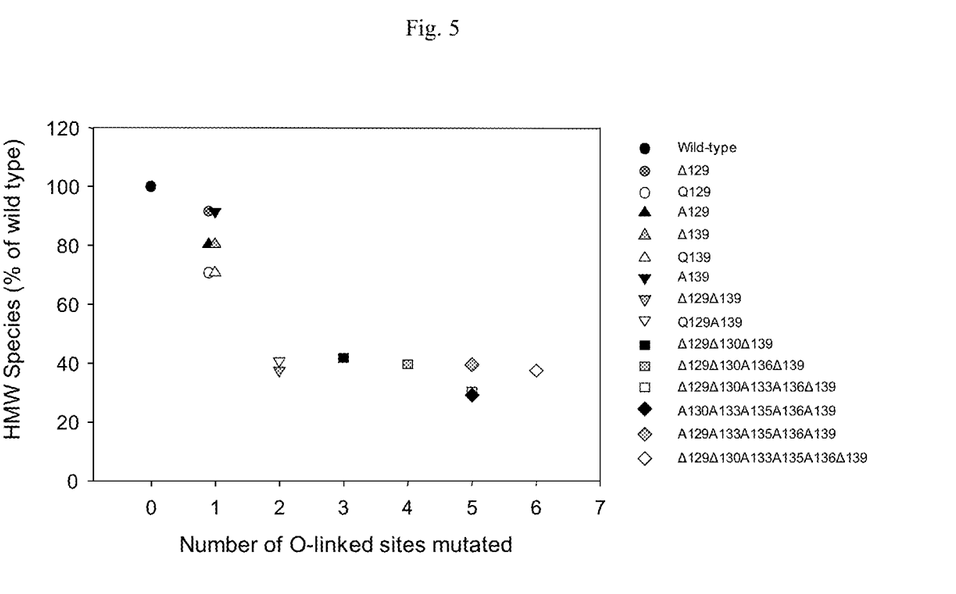
FIG. 5 shows the reduction in percentage of high molecular weight (HMW) species with respect to O-linked sites mutated; data normalized to 100% in wild type control. There were six potential O-linked sites and mutants were created to eliminate one to all six glycosylation sites.

Protein aggregation was reduced by eliminating O-linked sites through substitution or deletion judged by a significant reduction in the amount of HMW species in the protein products. Mutating either S129 or S139 caused a decrease in the percentage of HMW species ranging from 8% to 29% whereas mutating both caused a 60% decrease in HMW (FIG. 5). Eliminating three or more O-linked glycosylation sites did not further enhance reduction in HMW beyond what was seen in the double deletion mutants.

What is claimed is:

1. A mutant of the CTLA4Ig fusion protein set forth in SEQ ID NO: 2, wherein the mutant is a CTLA4Ig fusion protein as set forth in SEQ ID NO: 2 with deletion(s) and/or substitution(s) selected from the group consisting of:
   a) deletion of the serine at position 155 of SEQ ID NO: 2;
   b) substitution of the serine at position 155 of SEQ ID NO: 2 with a glutamine;
   c) substitution of the serine at position 155 of SEQ ID NO: 2 with an alanine;
   d) deletion of the serine at position 165 of SEQ ID NO: 2;
   e) substitution of the serine at position 165 of SEQ ID NO: 2 with a glutamine;
   f) substitution of the serine at position 165 of SEQ ID NO: 2 with an alanine;
   g) deletion of the serine at positions 155 and 165 of SEQ ID NO: 2;
   h) substitution of the serine at position 155 of SEQ ID NO: 2 with a glutamine and substitution of the serine at position 165 of SEQ ID NO: 2 with an alanine;
   i) deletion of the serine at positions 155, 156, and 165 of SEQ ID NO: 2;
   j) deletion of the serine at positions 155, 156, and 165 of SEQ ID NO: 2 and substitution of the serine at position 162 of SEQ ID NO: 2 with an alanine;
   k) deletion of the serine at positions 155, 156, and 165 of SEQ ID NO: 2 and substitution of the threonine at position 159 and the serine at position 162 of SEQ ID NO: 2 with an alanine;
   l) substitution of the serine at positions 156, 162, and 165 and the threonine at positions 159 and 161 of SEQ ID NO: 2 with an alanine;
   m) substitution of the serine at positions 155, 162, and 165 and the threonine at positions 159 and 161 of SEQ ID NO: 2 with an alanine; and
   n) deletion of the serine at positions 155, 156, and 165 of SEQ ID NO: 2 and substitution of the threonine at positions 159 and 161 and the serine at position 162 of SEQ ID NO: 2 with an alanine.

2. A method of reducing the amount of high molecular weight species present in a protein product comprising a CTLA4Ig fusion protein, comprising site-directed mutagenesis of O-linked glycosylation site(s) in the CTLA4lg fusion protein shown in SEQ ID NO: 2 by:
   a) deleting the serine at position 155 of SEQ ID NO: 2;
   b) substituting the serine at position 155 of SEQ ID NO: 2 with a glutamine;
   c) substituting the serine at position 155 of SEQ ID NO: 2 with an alanine;
   d) deleting the serine at position 165 of SEQ ID NO: 2;
   e) substituting the serine at position 165 of SEQ ID NO: 2 with a glutamine;
   f) substituting the serine at position 165 of SEQ ID NO: 2 with an alanine;
   g) deleting the serine at positions 155 and 165 of SEQ ID NO: 2;
   h) substituting the serine at position 155 of SEQ ID NO: 2 with a glutamine and substituting the serine at position 165 of SEQ ID NO: 2 with an alanine;
   i) deleting the serine at positions 155, 156, and 165 of SEQ ID NO: 2;
   j) deleting the serine at positions 155, 156, and 165 of SEQ ID NO: 2 and substituting the serine at position 162 of SEQ ID NO: 2 with an alanine;
   k) deleting the serine at positions 155, 156, and 165 of SEQ ID NO: 2 and substituting the threonine at position 159 and the serine at position 162 of SEQ ID NO: 2 with an alanine;
   l) substituting the serine at positions 156, 162, and 165 and the threonine at positions 159 and 161 of SEQ ID NO: 2 with an alanine;
   m) substituting the serine at positions 155, 162, and 165 and the threonine at positions 159 and 161 of SEQ ID NO: 2 with an alanine; or
   n) deleting the serine at positions 155, 156, and 165 of SEQ ID NO: 2 and substituting the threonine at positions 159 and 161 and the serine at position 162 of SEQ ID NO: 2 with an alanine;
   and then expressing the mutated CTLA4lg fusion protein.

* * * * *

UNITED STATES PATENT AND TRADEMARK OFFICE
CERTIFICATE OF CORRECTION

PATENT NO. : 9,926,365 B2  
APPLICATION NO. : 14/410709  
DATED : March 27, 2018  
INVENTOR(S) : Yueming Qian et al.

Page 1 of 1

It is certified that error appears in the above-identified patent and that said Letters Patent is hereby corrected as shown below:

In the Claims

Claim 2, Column 18, Line 3:
Delete "CTLA4lg" and insert -- CTLA4Ig --

Claim 2, Column 18, Line 4:
Delete "CTLA4lg" and insert -- CTLA4Ig --

Claim 2, Column 18, Line 40:
Delete "CTLA4lg" and insert -- CTLA4Ig --

Signed and Sealed this
Twenty-sixth Day of February, 2019

Andrei Iancu
*Director of the United States Patent and Trademark Office*

SEQUENCE LISTING

```
<160> NUMBER OF SEQ ID NOS: 5

<210> SEQ ID NO 1
<211> LENGTH: 1152
<212> TYPE: DNA
<213> ORGANISM: Artificial Sequence
<220> FEATURE:
<223> OTHER INFORMATION: Belatacept CTLA4Ig Mutant

<400> SEQUENCE: 1
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca aatatactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360
gagctcatgt acccaccgcc atactacgag ggcataggca acggaaccca gatttatgta     420
attgatccag aaccgtgccc agattctgat caggagccca aatcttctga caaaactcac     480
acatccccac cgtccccagc acctgaactc ctggggggat cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
```

-continued

| | |
|---|---|
| cataatgcca agacaaagcc gcgggaggag cagtacaaca gcacgtaccg tgtggtcagc | 720 |
| gtcctcaccg tcctgcacca ggactggctg aatggcaagg agtacaagtg caaggtctcc | 780 |
| aacaaagccc tcccagcccc catcgagaaa accatctcca aagccaaagg gcagccccga | 840 |
| gaaccacagg tgtacaccct gccccatcc cgggatgagc tgaccaagaa ccaggtcagc | 900 |
| ctgacctgcc tggtcaaagg cttctatccc agcgacatcg ccgtggagtg ggagagcaat | 960 |
| gggcagccgg agaacaacta caagaccacg cctcccgtgc tggactccga cggctccttc | 1020 |
| ttcctctaca gcaagctcac cgtggacaag agcaggtggc agcaggggaa cgtcttctca | 1080 |
| tgctccgtga tgcatgaggc tctgcacaac cactacacgc agaagagcct ctccctgtct | 1140 |
| ccgggtaaat ga | 1152 |

<210> SEQ ID NO 2
<211> LENGTH: 383
<212> TYPE: PRT
<213> ORGANISM: Artificial Sequence
<220> FEATURE:
<223> OTHER INFORMATION: Belatacept CTLA4Ig Mutant

<400> SEQUENCE: 2

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Tyr Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

```
Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
        290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
        325                 330                 335

Asp Gly Ser Phe Phe Leu Tyr Ser Lys Leu Thr Val Asp Lys Ser Arg
        340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
        370                 375                 380

<210> SEQ ID NO 3
<211> LENGTH: 19
<212> TYPE: PRT
<213> ORGANISM: Artificial Sequence
<220> FEATURE:
<223> OTHER INFORMATION: Mutated IgG hinge region with O-linked
      glycosylation site at S129, S130, S139
<220> FEATURE:
<221> NAME/KEY: MISC_FEATURE
<223> OTHER INFORMATION: Ser5, Ser6, Ser15, O-linked glycosylation sites

<400> SEQUENCE: 3

Gln Glu Pro Lys Ser Ser Asp Lys Thr His Thr Ser Pro Pro Ser Pro
1               5                   10                  15

Ala Pro Glu

<210> SEQ ID NO 4
<211> LENGTH: 19
<212> TYPE: PRT
<213> ORGANISM: Artificial Sequence
<220> FEATURE:
<223> OTHER INFORMATION: Mutated IgG hinge region with N-linked
      glycosylation site at S129, S130, T133, T135, S136, S139
<220> FEATURE:
<221> NAME/KEY: MISC_FEATURE
<223> OTHER INFORMATION: Ser5, Ser6,Thr9,Thr11, Ser12, Ser15, O-linked
      glycosylation sites

<400> SEQUENCE: 4

Gln Glu Pro Lys Ser Ser Asp Lys Thr His Thr Ser Pro Pro Ser Pro
1               5                   10                  15

Ala Pro Glu

<210> SEQ ID NO 5
<211> LENGTH: 28
<212> TYPE: PRT
<213> ORGANISM: Homo sapiens

<400> SEQUENCE: 5

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe
                20                  25
```